United States Patent
Banerjee et al.

(10) Patent No.: US 11,480,608 B2
(45) Date of Patent: Oct. 25, 2022

(54) SPACE TIME ELECTRON-HOLE CHARGE TRANSPORT NETWORK FOR SOLID-STATE MATERIAL STUDIES

(71) Applicant: Siemens Medical Solutions USA, Inc., Malvern, PA (US)

(72) Inventors: Srutarshi Banerjee, Chicago, IL (US); Miesher Rodrigues, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 363 days.

(21) Appl. No.: 16/850,231

(22) Filed: Apr. 16, 2020

(65) Prior Publication Data
US 2021/0133564 A1    May 6, 2021

Related U.S. Application Data

(60) Provisional application No. 62/929,203, filed on Nov. 1, 2019.

(51) Int. Cl.
*G06N 3/08* (2006.01)
*G01R 31/28* (2006.01)
*G06N 3/04* (2006.01)
*G01N 33/00* (2006.01)

(52) U.S. Cl.
CPC ....... *G01R 31/2831* (2013.01); *G06N 3/0481* (2013.01); *G06N 3/08* (2013.01); *G01N 2033/0095* (2013.01)

(58) Field of Classification Search
CPC .... G01R 33/443; G01R 33/5608; G06N 3/00; G06N 3/02
See application file for complete search history.

(56) References Cited

U.S. PATENT DOCUMENTS

| | | | |
|---|---|---|---|
| 10,656,962 B2 * | 5/2020 | Lin | G06N 3/063 |
| 2018/0276529 A1 * | 9/2018 | Paul | G06N 3/0454 |

OTHER PUBLICATIONS

Daniel C. Elton et al. Deep learning for molecular design—a review of the state of the art; arXiv:1903.04388v3 [cs.LG] (May 22, 2019); 1-24.

O. Caylak, A. Yaman, B. Baumeier, "Evolutionary Approach to Constructing a Deep Feedfoarward Neural Network for Prediction of Electronic Coupling Elements in Molecular Materials", JCTC, ; (2019) 1777-1784.

(Continued)

*Primary Examiner* — Tung X Nguyen

(57) ABSTRACT

A method of training a neural network modeling physical phenomena of semiconductor material includes receiving plurality of training pairs corresponding to a semiconductor material. Each training pair comprises an input charge to a distinct voxel of the semiconductor material and one or more output signals generated by the distinct voxel in response to the input charge. A neural network is trained using the training pairs. The neural network models the semiconductor material and each voxel is represented in the neural network by a tensor field defined by (i) a location of the voxel within the semiconductor material and (ii) one or more physics-based phenomena within the voxel at the location.

19 Claims, 10 Drawing Sheets

(56) References Cited

OTHER PUBLICATIONS

J. Lederer, W. Kaiser, A. Mattoni, A. Gagliardi, "Machine Learning-Based Charge Transport Computation for Pentacene", Advanced Theory and Simulations; Adv Theory Simul. (2018), 1800136; 1-11.
T. Hamilton and H. Mohseni, "Space-Time Scattering Network for Electromagnetic Inverse Design and Tomography"; Department of Electrical Engineering, Northwestern University, Evanston, IL 1-5.
He, Zhong. "Review of the Shockley-Ramo theorem and its application in semiconductor gamma-ray detectors." Nuclear Instruments and Methods in Physics Research A 463 (2001) 250-267.

* cited by examiner

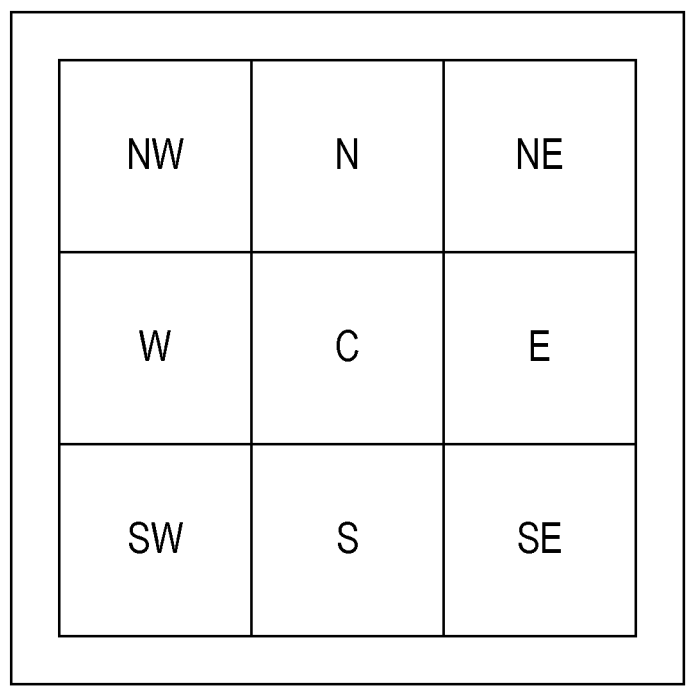
Cathode Side
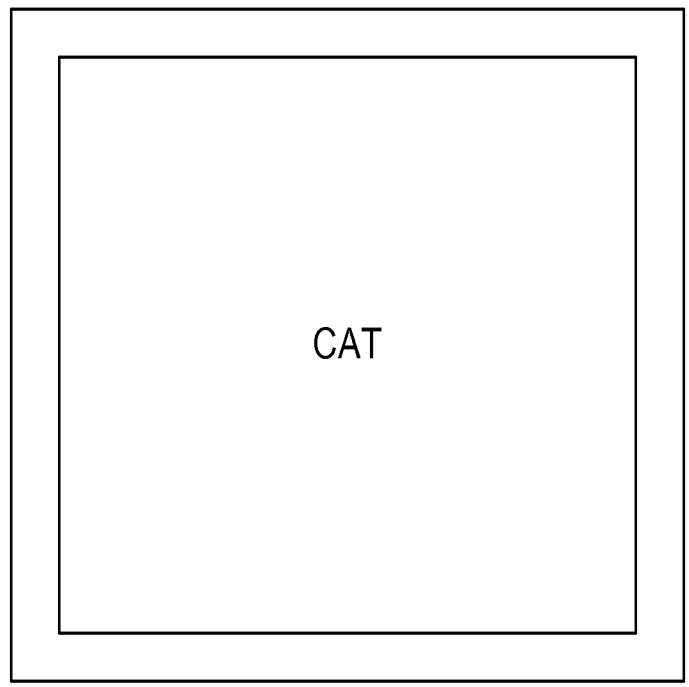
Anode Side
*Fig. 1A*

| Property | Material "1" | Material "2" |
|---|---|---|
| Mobility of free electrons [cm²/V/s] | 1000 | |
| Mobility of free holes [cm²/V/s] | 50 | |
| Diffusion coefficient of free electrons [cm²/s] | 18.975 | |
| Diffusion coefficient of free holes [cm²/s] | 1.265 | |
| Probability of electrons trapping into defect level "1" [%] | 10 | 0 |
| Probability of electrons detrapping from defect level "1" [%] | 20 | 100 |
| Probability of holes trapping into defect level "1" [%] | 10 | 0 |
| Probability of holes detrapping from defect level "1" [%] | 1 | 100 |
| Probability of holes trapping into defect level "2" [%] | 20 | 0 |
| Probability of holes detrapping from defect level "2" [%] | 1 | 100 |

*Fig. 1B*

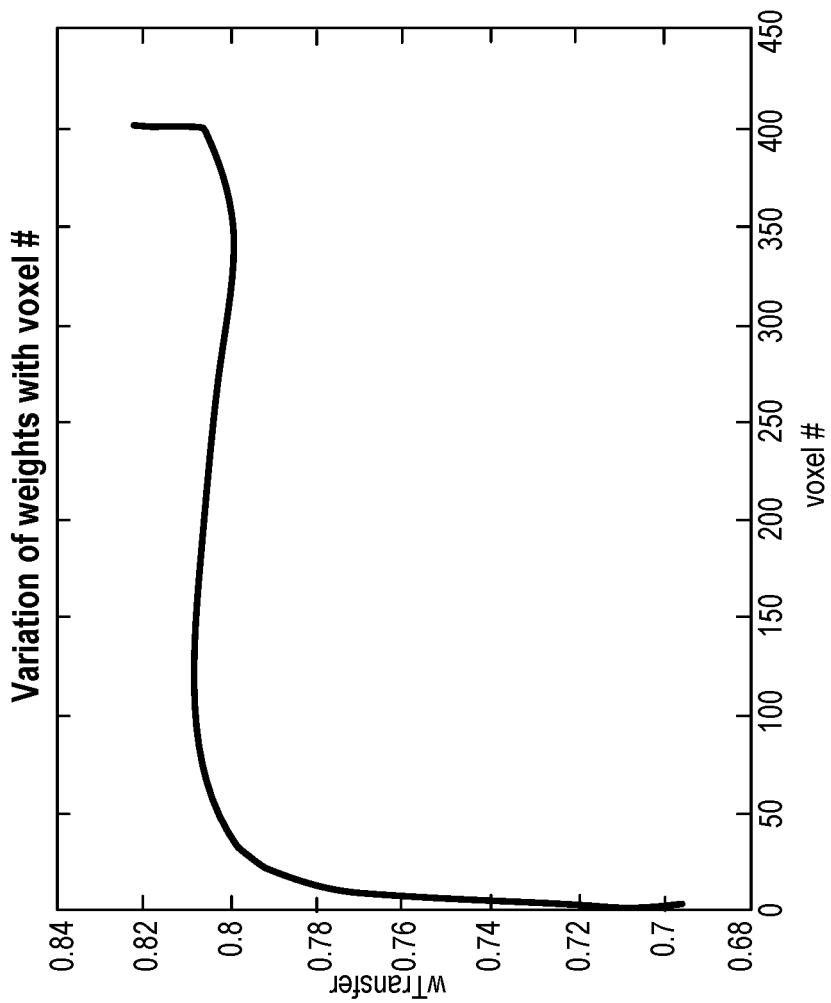

SPACE TIME ELECTRON-HOLE CHARGE TRANSPORT NETWORK FOR SOLID-STATE MATERIAL STUDIES

CROSS-REFERENCE TO RELATED APPLICATIONS

This application claims the benefit of U.S. Provisional Application Ser. No. 62/929,203 filed Nov. 1, 2019, which is incorporated herein by reference in its entirety.

TECHNICAL FIELD

The present invention relates generally to computer-based methods, systems, and apparatuses generally to machine learning and more specifically to a space time electron-hole charge transport network. The technology described herein may be applied, for example, to perform studies of medical imaging detectors and other semiconductor materials.

BACKGROUND

Solid-state semiconductor materials like silicon have unique properties due to the very regular crystal lattice structure of the material. These properties make such materials vital to many applications where electronics technology is used. For example, in the medical field, detectors on imaging devices such as CT, SPECT and X-ray scanners have been proposed with solid-state materials. The specifications of the solid-state materials used in different applications may vary with respect to electron and hole transport properties. In order to determine if a material is suitable for a particular application, typically an expert must perform a thorough material characterization using specialized equipment and expertise.

Development of solid-state devices relies on detailed measurement and characterization of different semiconductor material properties. The scope of these measurements is usually defined by a fine balance between available resources and time. Of course, anything can be measured to the infinitesimal degree of precision and accuracy if unlimited resources and time are available. In reality, this never happens.

The characterization of solid-state detectors in literature, so far has been done by numerous experimental measurements and simulations using dedicated equipment for each of these measurements. A major limitation of such conventional methods is that materials can only be characterized as a single or a couple of properties in the bulk. It is challenging, if not impossible, to have a detailed description of the material properties on a voxel-by-voxel basis for voxel sizes in micrometer scale. Moreover, the resource and time required to achieve more detailed results using conventional measurements are not justifiable. It is currently impossible to execute a detailed characterization of semiconductors in micrometer scale with the resources and time available.

Analytical solutions for solving nonlinear transport equations in semiconductors are performed using numerical methods. Conventional methods of solving the problem of charge transport using neural networks are very limited. For example, one conventional method is to use an evolutionary approach to construct a Deep Feedforward Neural Network for Prediction of Electronic Coupling Elements in Molecular Materials. A Genetic Algorithm optimizes the number of hidden layers and neurons in each hidden layer of the feedforward network. A second conventional technique applies a machine learning-based multiscale method for computation of charge transport properties focusing on prediction of electronic transfer integrals.

These conventional analytical solutions have the significant limitation of being unable to find the material properties along the bulk of the material. The material properties are assumed to be constant across the bulk. Another neural network method of prediction depends on finding too many weights which increases the training time and in turn solving for the parameters (weights) has no direct relation with the material properties themselves, such as mobility, trapping lifetime, de-trapping lifetime, etc.

SUMMARY

Embodiments of the present invention address and overcome one or more of the above shortcomings and drawbacks, by providing methods, systems, and apparatuses related to a space time electron-hole charge transport network for solid-state material studies.

In some embodiments, a method of training a neural network modeling physical phenomena of semiconductor material includes receiving plurality of training pairs corresponding to a semiconductor material. Each training pair comprises an input charge to a distinct voxel of the semiconductor material and one or more output signals generated by the distinct voxel in response to the input charge. A neural network is trained using the training pairs. The neural network models the semiconductor material and each voxel is represented in the neural network by a tensor field defined by (i) a location of the voxel within the semiconductor material and (ii) one or more physics-based phenomena within the voxel at the location.

According to another aspect of the present invention, in some embodiments, the neural network comprises a plurality of weights transforming input data to nodes of the neural network and each of the weights models one or more physics-based phenomena related to the semiconductor material. For example, the weights may model one or more transport of electrons and holes in the semiconductor material, trapping and de-trapping of electrons and holes in the semiconductor material, recombination of electrons and holes in the semiconductor material, and diffusion of electrons and holes in the semiconductor material. In one embodiment, the weights are modeled using a plurality of tensors and each tensor corresponds to one of the physics-based phenomena. The weights may be optimized during the training, for example, using a gradient descent algorithm based on a loss function.

In other embodiments, a method of training a neural network modeling physical phenomena of a semiconductor material includes receiving an input charge measurement and generating a voxel-by-voxel description of a semiconductor's material properties by applying the input charge measurement to a trained neural network. The trained neural network comprises a plurality of weights transforming input data to nodes of the trained neural network. Each of the weights models one or more physics-based phenomena related to the semiconductor material. The method may further include displaying at least a portion of the voxel-by-voxel description of the semiconductor's material properties in a graphical user interface.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, they are shown in the drawings embodiments that are presently preferred, it being understood, however, that the invention is not limited to the specific instrumentalities disclosed. Included in the drawings are the following Figures:

FIG. 1A shows an electrode pattern on a semiconductor detector, according to some embodiments;

FIG. 1B shows a table with properties for two slightly different materials with the electrode configuration shown in FIG. 1A;

FIG. 4 is a plot that shows the transfer weights as a function of voxel, according to some embodiments;

DETAILED DESCRIPTION

Figure 1C:
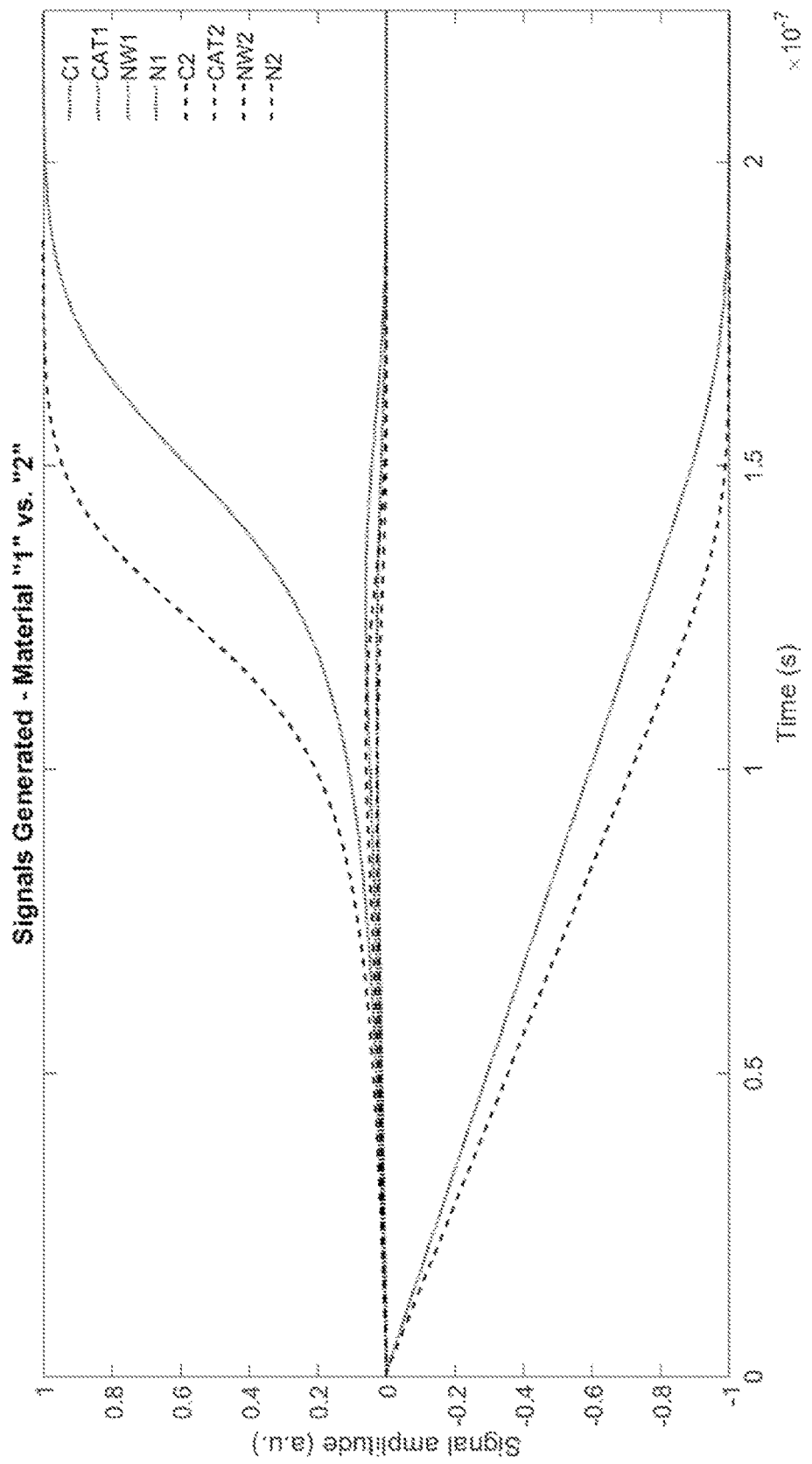
FIG. 1C shows the signals corresponding an electrode pattern on a semiconductor detector, according to some embodiments.

Systems, methods, and apparatuses are described herein which relate generally to a space time electron-hole charge transport network for solid-state material studies. Briefly, the problem of measuring semiconductor material properties is modeled as a physics-based neural network with weights that are directly related with the physical properties of the material. The characteristics of the material are obtained by solving for the weights in an inverse manner. The techniques disclosed herein uses the output signals and input charges to optimize the weights of the model. This forms a training pair. The more training pairs utilized, the closer are the weights to the predicted values. According to some embodiments, a gradient descent based approach is taken to optimize the weights of the model based on the loss function computation in each step.

In solid-state devices, the properties of the flow of electric current through the material, commonly referred to as charge transport, plays a significant role in determining if one material is better suited for an application. For example, CdZnTe detectors are known to be plagued by shallow defect levels. Conventional compensation techniques used to increase the resistivity of CdZnTe detectors introduce deep defect levels in the material. In turn, the deeper defects act as trapping centers, trapping free carriers for longer times, degrading the performance of the detectors.

Semiconductor radiation detectors and other solid-state materials are typically characterized by finding the material properties that are relevant to quantify the transport of charges inside the material, i.e., electrons and holes charge mobility $\mu_e$ and $\mu_h$; electrons and holes trapping times for M electrons and N holes trapping centers, $\tau_{e1}, \tau_{e2}, \tau_{e3}, \ldots, \tau_{eM}$ and $\tau_{h1}, \tau_{h2}, \tau_{h3}, \ldots, \tau_{hN}$; and electrons and holes de-trapping for M electrons and N holes de-trapping centers, $\tau_{de1}, \tau_{de2}, \tau_{de3}, \ldots, \tau_{deM}$ and $\tau_{dh1}, \tau_{dh2}, \tau_{dh3}, \ldots, \tau_{dhN}$. De-trapping times can be converted into defect energy levels, such that shallow traps correspond to shorter de-trapping times while deeper traps correspond to longer de-trapping times. Trapping times are related to the density of traps in the material for both electrons and holes. At a microscopic level, the overall effect is observed as a hopping mechanism of charge transport for both electrons and holes. These charges are driven by the electric field until collected by corresponding electrodes and signals are induced in these electrodes due to the movement of these charges. The coupled system of equations that represent charge transport can be written as:

$$\frac{\partial n_e}{\partial t} + \nabla \cdot (n_e \mu_e \cdot \nabla \phi) - \nabla \cdot (D_e \cdot \nabla n_e) =$$
$$-\frac{n_e}{\tau_{et1}} + \frac{\tilde{n}_{e1}}{\tau_{ed1}} - \frac{n_e}{\tau_{et2}} + \frac{\tilde{n}_{e2}}{\tau_{ed2}} - \ldots \ldots - \frac{n_e}{\tau_{etN}} + \frac{\tilde{n}_{eN}}{\tau_{edN}} + \delta_e$$

$$\frac{\partial n_h}{\partial t} + \nabla \cdot (n_h \mu_h \cdot \nabla \phi) - \nabla \cdot (D_h \cdot \nabla n_h) =$$
$$-\frac{n_h}{\tau_{ht1}} + \frac{\tilde{n}_{h1}}{\tau_{hd1}} - \frac{n_h}{\tau_{ht2}} + \frac{\tilde{n}_{h2}}{\tau_{hd2}} - \ldots \ldots - \frac{n_h}{\tau_{htP}} + \frac{\tilde{n}_{hP}}{\tau_{hdP}} + \delta_h$$

$$\frac{\partial \tilde{n}_{e1}}{\partial t} = \frac{n_e}{\tau_{et1}} - \frac{\tilde{n}_{e1}}{\tau_{ed1}}$$

$$\frac{\partial \tilde{n}_{e2}}{\partial t} = \frac{n_e}{\tau_{et2}} - \frac{\tilde{n}_{e2}}{\tau_{ed2}}$$

$$\vdots$$

$$\frac{\partial \tilde{n}_{eN}}{\partial t} = \frac{n_e}{\tau_{etN}} - \frac{\tilde{n}_{eN}}{\tau_{edN}}$$

$$\frac{\partial \tilde{n}_{h1}}{\partial t} = \frac{n_h}{\tau_{ht1}} - \frac{\tilde{n}_{h1}}{\tau_{hd1}}$$

$$\frac{\partial \tilde{n}_{h2}}{\partial t} = \frac{n_h}{\tau_{ht2}} - \frac{\tilde{n}_{h2}}{\tau_{hd2}}$$

$$\vdots$$

$$\frac{\partial \tilde{n}_{hP}}{\partial t} = \frac{n_h}{\tau_{htP}} - \frac{\tilde{n}_{hP}}{\tau_{hdP}}$$

$$D_e = \mu_e \frac{kT}{e}$$

$$D_h = \mu_h \frac{kT}{e}$$

where, $n_e$: free electron concentration in excess of equilibrium $n_h$: free hole concentration in excess of equilibrium $\tilde{n}_{eN}$: trapped electron concentration in defect level N=1, 2, ...

$\tilde{n}_{hP}$: trapped hole concentration in defect level P=1, 2, ...

$\tau_{etN}$: electron trapping lifetime in defect level N=1, 2, ...

$\tau_{htP}$: hole trapping lifetime in defect level P=1, 2, ...

$\mu_e$: mobility of free electrons $\mu_h$: mobility of free holes $D_e$: diffusion coefficient of free electrons $D_h$: diffusion coefficient of free holes $\delta_e$: electron source term $\delta_h$: hole source term $\emptyset$: electrical potential e: charge of an electron and other terms, $$\nabla^2 \phi = -k\frac{e}{\varepsilon_0}(n_e + \tilde{n}_{e1} + \tilde{n}_{e1} + \tilde{n}_{e2} + \ldots + \tilde{n}_{e2} + n_h + \tilde{n}_{h1} + \tilde{n}_{h2} + \ldots + \tilde{n}_{hP})$$

where, $$E = -\nabla \phi$$

At a microscopic level, the system described by the above equations is analytically solved with the source $\delta_e$ and $\delta_h$ given by the electron-hole pairs generated by photon interactions in the material or by other types of interactions, where the number of electrons and holes initially created is proportional to the material band-gap. The various trapping and de-trapping levels of electrons and holes are considered. A history of previous time steps is recorded as a function of time. Also, the effect of recombination between electrons and holes amongst different trap levels and charges in conduction and valence bands is calculated. In addition, electron and hole charge diffusion is also solved in the model.

Signals measured in solid-state detectors arise from the drift of charges moving in the bulk of the material, i.e., electrons and holes. These signals can be measured using a charge-sensitive amplifier with the addition of other analog and digital electronics. For example, FIG. 1A shows an electrode pattern on a semiconductor detector (CdZnTe) showing 09 (nine) electrodes (NW,N,NE,W,C,E,SW,S and SE) on the anode side, and a single large electrode on the cathode side (CAT). FIG. 1B shows a table with properties for two slightly different materials with the electrode configuration shown in FIG. 1A. FIG. 1C shows the signals simulated corresponding an electrode pattern on a semiconductor detector (CdZnTe) showing 09 (nine) electrodes (NW,N,NE,W,C,E,SW,S and SE) on the anode side, and a single large electrode on the cathode side (CAT).

In contrast to conventional, analytical solutions for solving the nonlinear transport equations set out above, the techniques described herein formulate the transport problem in a neural network framework that incorporates the underlying laws of physics. This neural network framework applies deep learning methods to use multiple layers of the neural network framework to progressively extract phenomenon related to semiconductor evaluation from the raw input. The physics-based neural network described herein may be implemented, for example, by Tensorflow™ (by Google) or PyTorch (by Facebook) on a CPU/GPU computing platform for forward modeling. One example CPU/GPU computing platform is described below with reference to FIG. 6.

The physics-based neural network discussed herein address four phenomena related to semiconductor evaluations: transport of electrons and holes; trapping and de-trapping of electrons and holes; recombination of electrons and holes; and diffusion of electrons and holes. Each of the phenomena is modeled in the neural network framework as one or more weights. As is generally understood in the art, the basic unit of computation in a neural network is the node that receives inputs from other nodes in the network. Each input to the neuron is assigned a weight on the basis of that input's importance relative to other inputs to the neuron. Weights are learned during the training process. The physics-based neural network described herein is trained using a pair of output signals (from the electrodes) as well as input charge to a discrete element of the material (referred to herein as a "voxel"). The physics-based neural network determines the weights which are identical to the exact parameters estimated from simulation and theoretical calculations. In some embodiments, the loss function for training the physics-based neural network is calculated using the L2 norm of the difference between the output training signals and the signals generated by the neural network. In other embodiments, other formulations of the loss function may be used.

The semiconductor material is assumed to be composed of N number of voxels. This represents a discretization of the sensor in the space. The semiconductor material has a cathode on one end and anode on the other end in space. Charges move from the electrode of one polarity to another—i.e., the electrons move from cathode to anode and holes move from anode to cathode. While the charges transport, the phenomenon of transport, diffusion, trapping, de-trapping and recombination occurs. Assuming causality holds, voxels may be modeled as nodes in space and time, which leads to the formation of "static" space-time fabric. Ideally, the dimensions of the voxel should be as small as possible. However, voxel size is inversely proportional to the computational time required to execute the physics-based neural network. Thus, the dimensions of each voxel can be selected to allow the physics-based neural network to execute within a desired run time.

Figure 2:
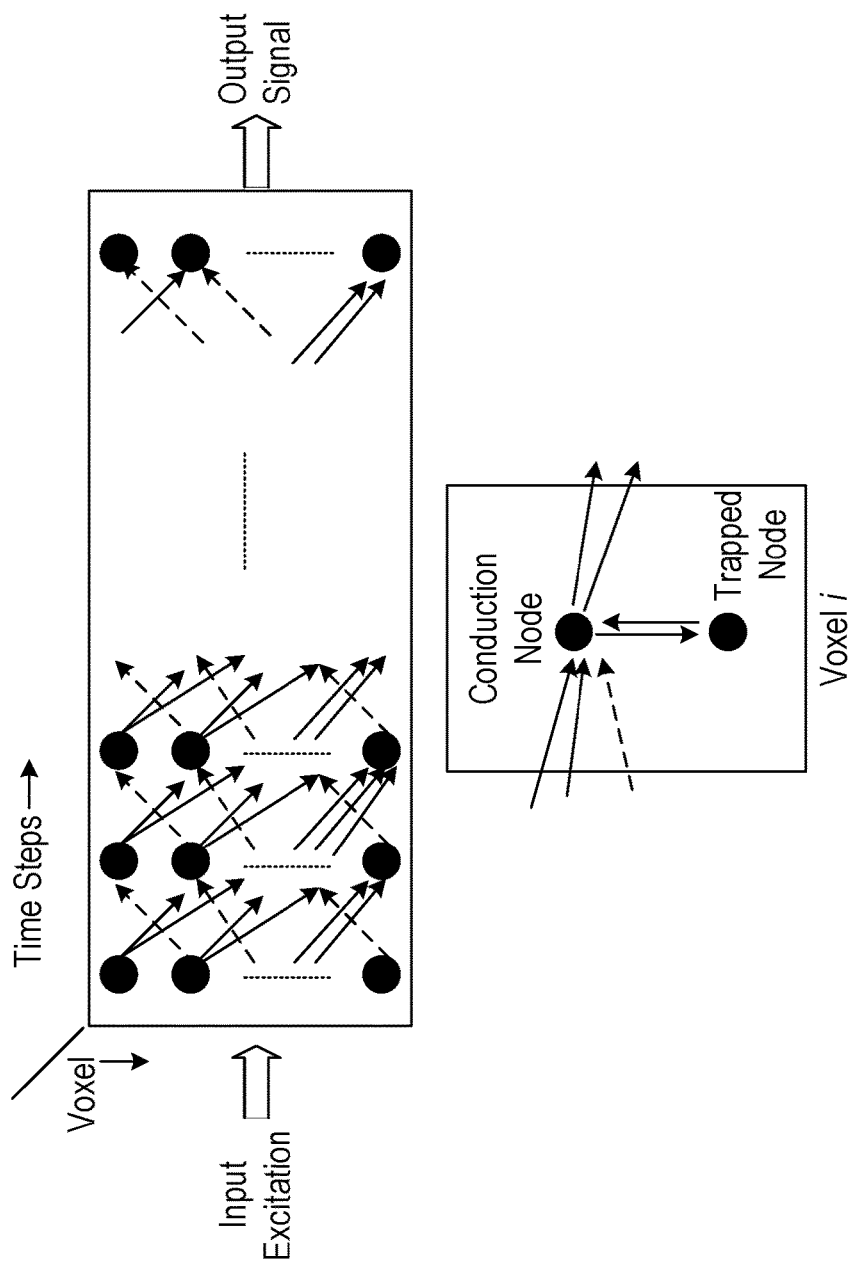
FIG. 2 shows a conceptual view of the space-time model of a semiconductor material that forms the basis of the physics-based neural network, according to some embodiments.

FIG. 2 shows a conceptual view of the space-time model of a semiconductor material that forms the basis of the physics-based neural network, according to some embodiments. The top image in FIG. 2 shows how charges propagate between voxels over time. Note that the arrows are going up and down because there are electrons and holes that move in opposite directions. As shown in the bottom image in FIG. 2, each voxel comprises a conduction node and a trapped node, just as in the physical model. The conduction node facilitates movement of the charge between voxels, while the trapped node traps the charge within the voxel (as depicted by the arrows between the conduction and trapped nodes. Each voxel has a different response that is dependent on the number of trapping centers present in the material. Thus, although this simplified example shows a single conduction node and a single trapped node, it should be understood that a voxel may have multiple trapped nodes based on the properties of the material.

Figure 3:
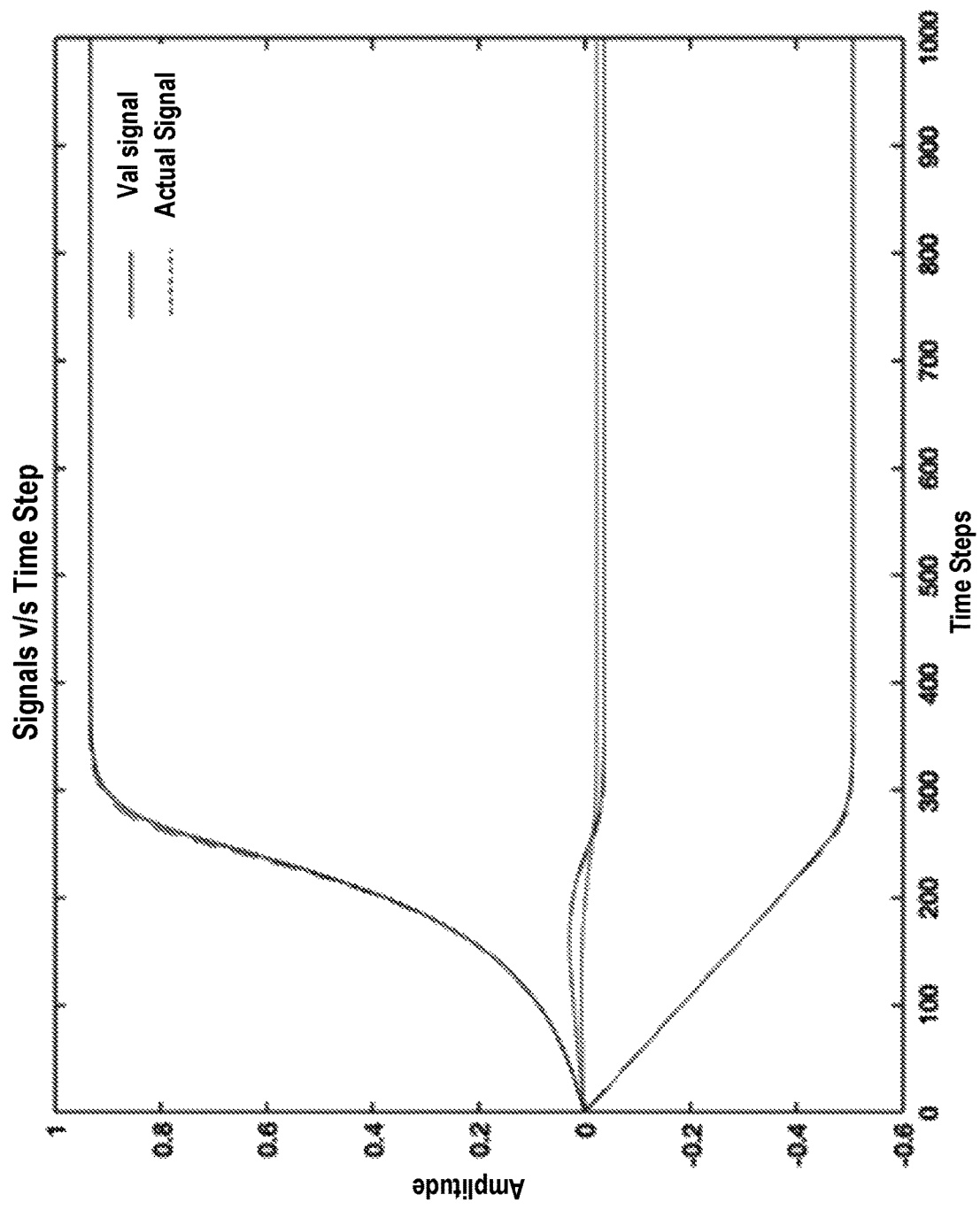
FIG. 3 shows simulated and actual signals for a voxel, according to some embodiments.

FIG. 3 shows simulated and actual signals for a voxel using the physics-based neural network described herein according to some embodiments. This figure depicts the different signals in different electrodes. The solid line is the signal that is received as an output of the physics-based neural network using a sample training set, and the dotted line is the ground truth. FIG. 4 is a plot that shows the transfer weights as a function of voxel. The transfer weight is correlated with the electric field within the material. The distribution of electric field is a function of position.

The physics-based neural network may be constructed in two phases. First, the network is developed in one-dimensional space and then, the network is expanded in higher dimensional space. As noted above, each of the phenomena (i.e., transport, diffusion, trapping, de-trapping and recombination) is described as a tensor field.

Figure 5A:
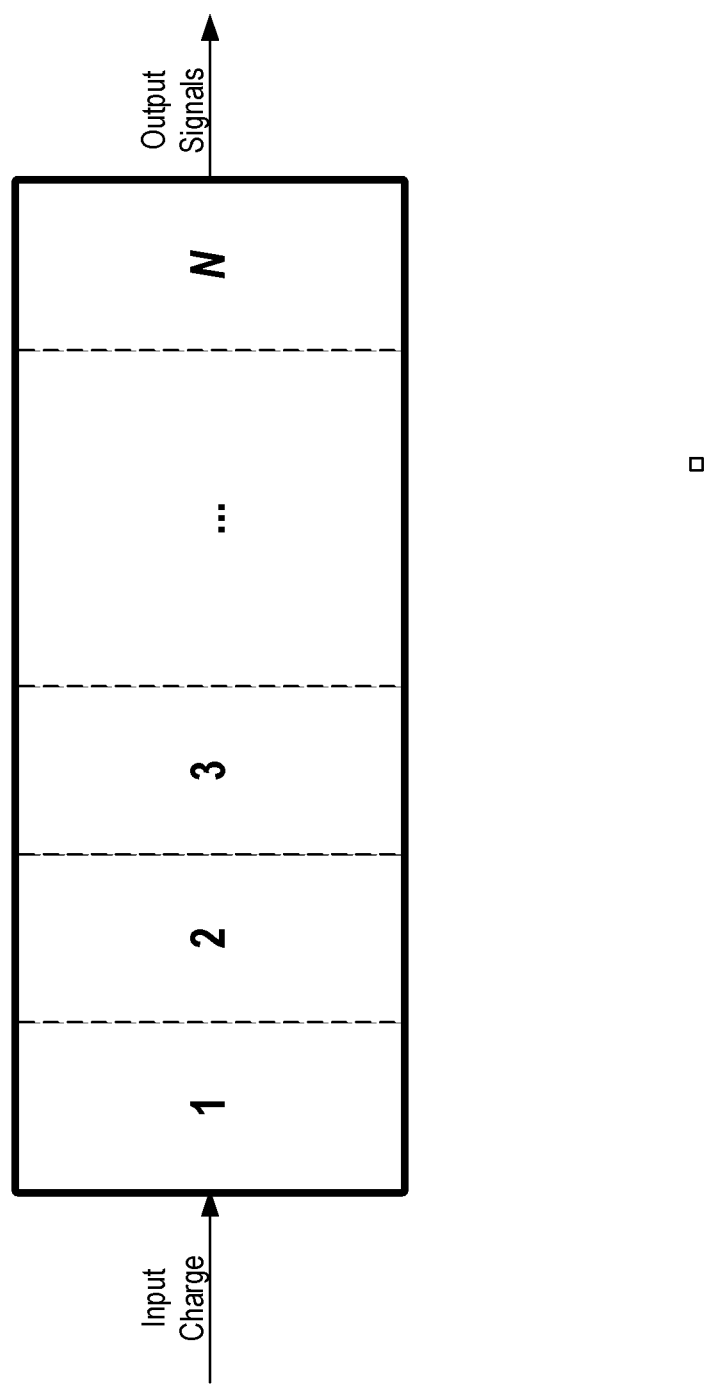
FIG. 5A show the voxel orientation in one dimension, according to some embodiments.
Figure 5B:
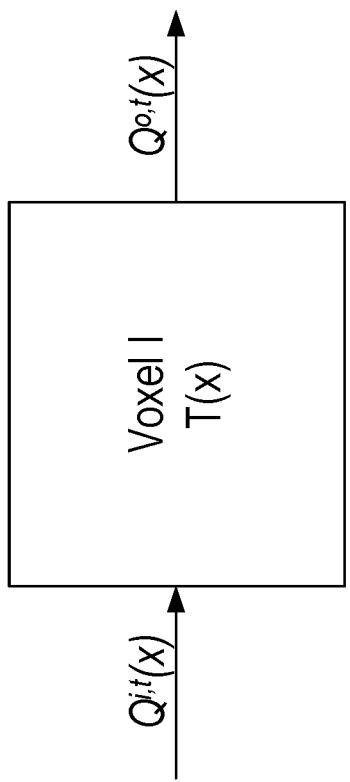
FIG. 5B shows the tensor in one voxel, according to some embodiments.
Figure 5C:
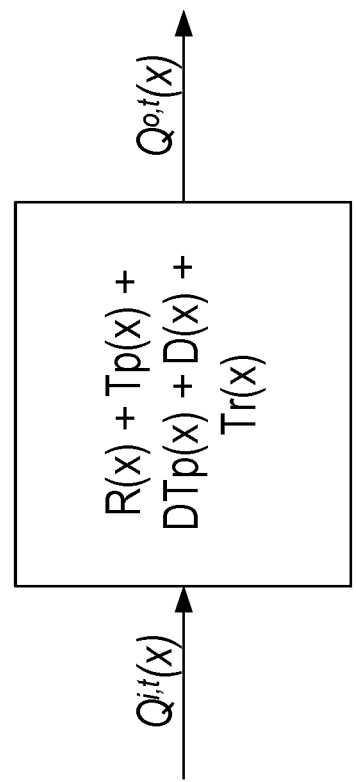
FIG. 5C shows an alternate view of the tensor in one voxel, according to some embodiments.

The incoming and outgoing charges, which are compactly written herein as $Q^{i,t}(x)$ and $Q^{o,t}(x)$, are coupled with a tensor field $T(x)$ at each voxel location at a given position x inside the material. The charges comprise electrons and holes which are propagating in opposite directions. The tensor field $T(x)$ is composed of several tensors, referred to herein as sub-tensors. The transport of charges is mathematically represented by a tensor field $Tr(x)$ at a location given by position x. The trapping of charges is represented by tensor field Tp(x), de-trapping of charges by tensor field DTp(x), diffusion of charges by tensor field D(x), and recombination of electrons and holes by R(x). The tensor field τ at a given location is represented as a subnet and is the basic building block of the network. The sub-tensors are combined using mathematical operations in order of the phenomena occurring within each voxel—recombination, trapping, de-trapping, diffusion and transport. The forward direction of electron propagation is positive x direction. So, the forward direction of hole propagation is in negative x direction. The tensor fields for electrons and holes differ spatially. FIG. 5A shows the voxel orientation in one dimension, while FIGS. 5B and 5C show the tensor in one voxel in three-dimensions.

The number of unknown weights in the physics-based neural network is exactly equal to the number of unknown parameters in the material (i.e., the number of parameters in the design space). This is the minimum possible parameters of unknown weights. This is in stark contrast with the conventional, non-physics based neural networks where the number of weights is typically much greater (many orders of magnitude) than the number of parameters in the design space. The training time for the conventional, non-physics based neural networks are orders of magnitude higher than the physics-based neural network described herein.

The sub-tensors comprise weights both inside a voxel i, as well as between a particular voxel i with surrounding voxels. This might be thought of analogous to a Long Short-Term Memory (LSTM)/Grated Recurrent Units (GRU) configuration for a particular voxel. However, instead of having a LSTM cell, the weights within each voxel is driven by physics based phenomena—i.e., trapping and de-trapping from the shallow and deep electron levels along with recombination of electrons and holes.

Figure 5D:
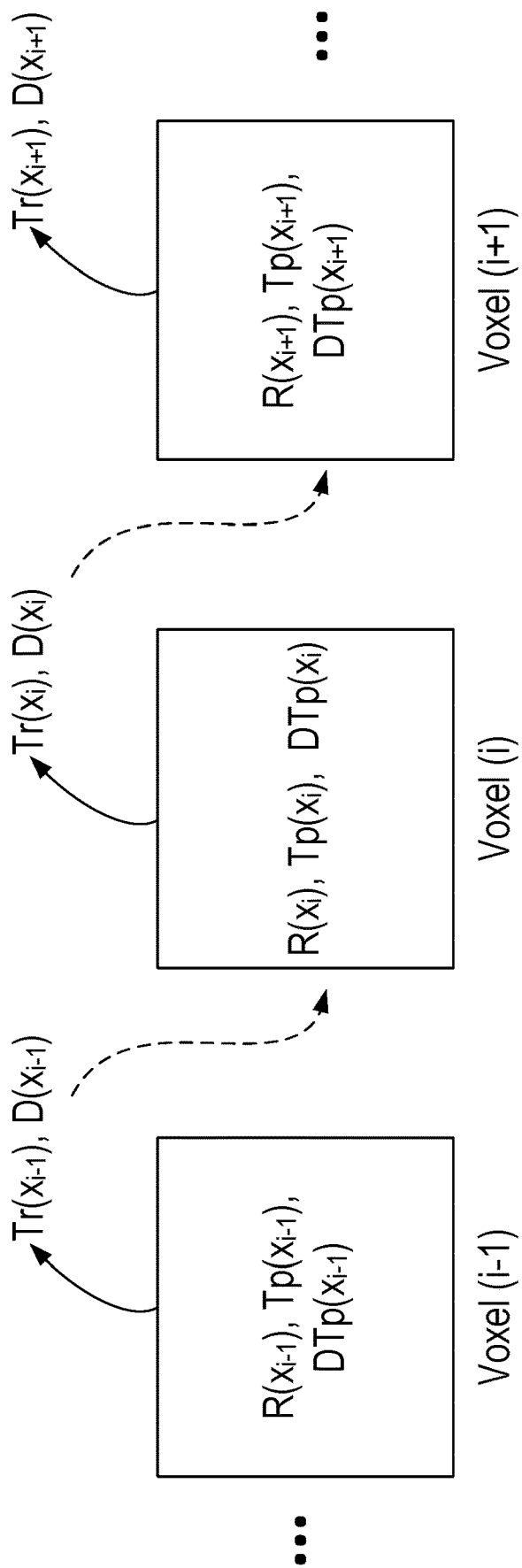
FIG. 5D shows sub-tensors and voxels illustrating this concept.

FIG. 5D shows sub-tensors and voxels illustrating this concept. Inside each of the voxel i, $R(x_i)$, $Tp(x_i)$ and $DTp(x_{i+1})$ occurs while $Tr(x_i)$, $D(x_i)$ represent the diffusion and transport of electrons and holes from one voxel i to neighboring voxels. Since the transport and diffusion of electrons and holes are in opposite directions, each voxel stores the amount of charge due to the electron and due to holes. For example, the transport $Tre(x_i)$ of the electrons is considered to be 5 voxels to the forward x direction, while the transport $Trh(x_i)$ of the holes is considered 2 voxels to the negative x direction. The transport sub-tensor $Tr(x_i)$ is thus a concatenation of $Tre(x_i)$ and $Trh(x_i)$. The diffusion parameters are similarly concatenated. For example, electrons diffuses by 2 voxels in the forward x direction $De(x_i)$ while the holes diffuses by 1 voxel to the negative x direction.

It should be noted that the physics-based neural network described herein does not require several experimental set-ups or numerous simulations in order to estimate the material properties, as in conventional techniques. Thus, the physics-based neural network provides an easy way of estimating the microscopic properties of the detector but with the numerical accuracy close to simulations. The physics-based neural network optimizes itself based on the gradient descent steps depending only on output signals and input charge in the voxels. The boundary conditions drive it to the optimal value of weights which are the material properties. The optimization may be performed based only on the signals without using complicated measurements.

This technique of characterizing the material will increase the ability to identify the material properties and defects in the solid-state materials, including semiconductor detectors. This will, in turn, allow the optimization of materials for an application. This will also reduce wastage of solid-state materials in some applications, where better characterization of defect levels enable the use of materials with lower quality having more defects in them. Finally, all over these benefits combine to provide a cost saving in materials testing in comparison to conventional techniques.

Figure 6:
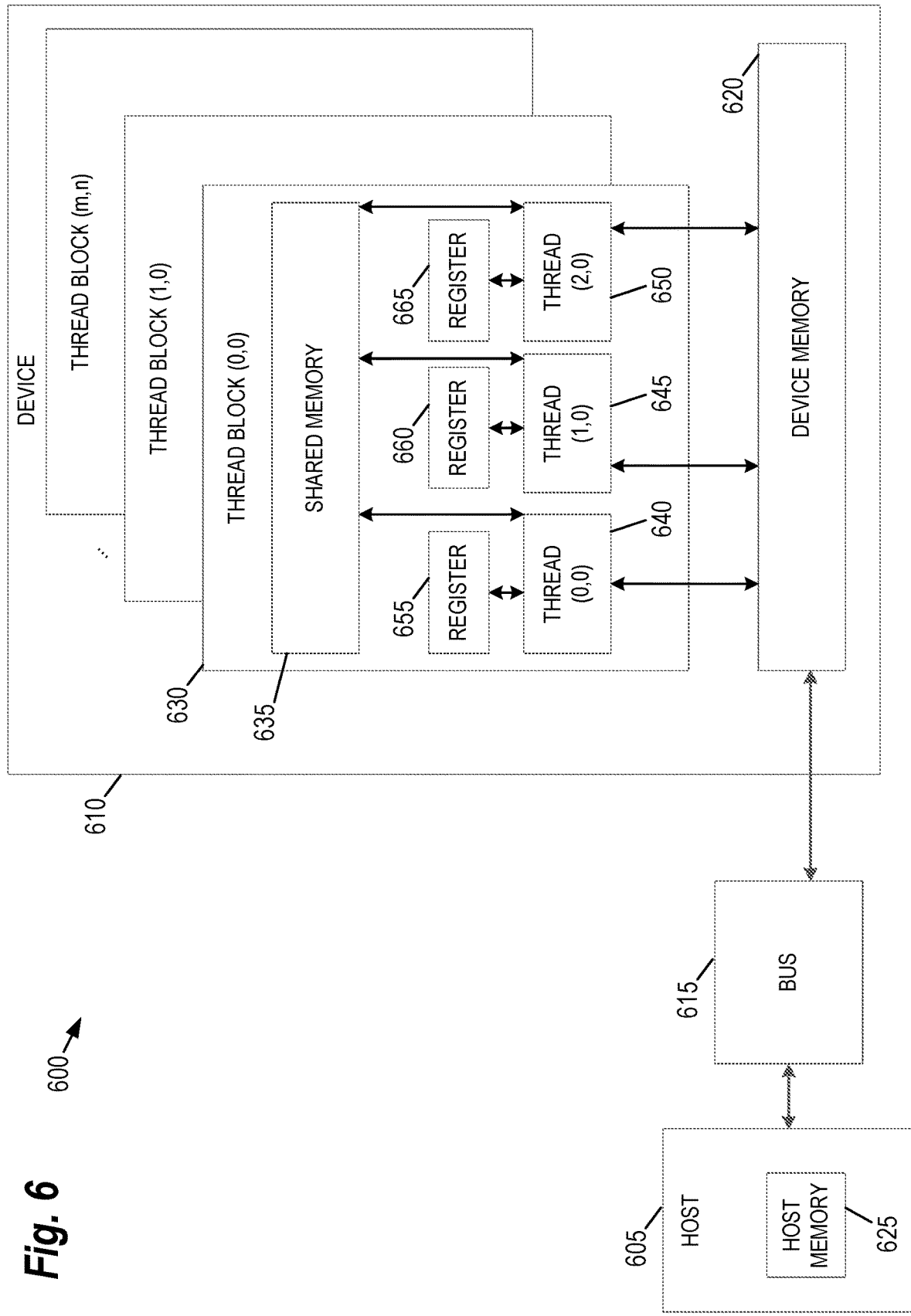
FIG. 6 provides an example of a parallel processing memory architecture that may be utilized to train or execute the physics-based neural network, according to some embodiments.

FIG. 6 provides an example of a parallel processing memory architecture 600 that may be utilized to train or execute the physics-based neural network discussed above. This architecture 600 may be used in embodiments of the present invention where NVIDIA™ CUDA (or a similar parallel computing platform) is used. The architecture includes a host computing unit ("host") 605 and a GPU device ("device") 610 connected via a bus 615 (e.g., a PCIe bus). The host 605 includes the central processing unit, or "CPU" (not shown in FIG. 6) and host memory 625 accessible to the CPU. The device 610 includes the graphics processing unit (GPU) and its associated memory 620, referred to herein as device memory. The device memory 620 may include various types of memory, each optimized for different memory usages. For example, in some embodiments, the device memory includes global memory, constant memory, and texture memory.

Parallel portions of the training algorithms may be executed on the architecture 600 as "device kernels" or simply "kernels." A kernel comprises parameterized code configured to perform a particular function. The parallel computing platform is configured to execute these kernels in an optimal manner across the architecture 600 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by grid of thread blocks (described in greater detail below). Using concurrent kernel execution, streams, and synchronization with lightweight events, the architecture 600 of FIG. 6 (or similar architectures) may be used to parallelize training tasks. For example, in some embodiments, processing of different nodes of the physics-based neural network.

The device 610 includes one or more thread blocks 630 which represent the computation unit of the device 610. The term thread block refers to a group of threads that can cooperate via shared memory and synchronize their execution to coordinate memory accesses. For example, in FIG. 6, threads 640, 645 and 650 operate in thread block 630 and access shared memory 635. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 6, the thread blocks 630 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints. In some embodiments, processing of subsets of the training data or operations performed by the algorithms discussed herein may be partitioned over thread blocks automatically by the parallel computing platform software. However, in other embodiments, the individual thread blocks can be selected and configured by the user to optimize training of the physics-based neural network.

Continuing with reference to FIG. 6, registers 655, 660, and 665 represent the fast memory available to thread block 630. Each register is only accessible by a single thread. Thus, for example, register 655 may only be accessed by thread 640. Conversely, shared memory is allocated per thread block, so all threads in the block have access to the same shared memory. Thus, shared memory 635 is designed to be accessed, in parallel, by each thread 640, 645 and 650 in thread block 630. Threads can access data in shared memory 635 loaded from device memory 620 by other threads within the same thread block (e.g., thread block 630). The device memory 620 is accessed by all blocks of the grid and may be implemented using, for example, Dynamic Random-Access Memory (DRAM).

Each thread can have one or more levels of memory access. For example, in the architecture 600 of FIG. 6, each thread may have three levels of memory access. First, each thread 640, 645, 650, can read and write to its corresponding registers 655, 660, and 665. Registers provide the fastest memory access to threads because there are no synchronization issues and the register is generally located close to a multiprocessor executing the thread. Second, each thread 640, 645, 650 in thread block 630, may read and write data to the shared memory 635 corresponding to that block 630. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 610 to read and/or write to the device memory 620. Device memory 620 requires the longest time to access because access must be synchronized across the thread blocks operating on the device. Thus, in some embodiments, the processing of each node of the physics-based neural network is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 6, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions a computing system's processor to generate signals representing the GUI display images. The processor, under control of an executable procedure or executable application, manipulates the GUI display images in response to signals received from the input devices. In this way, the user may interact with display images using the input devices, enabling user interaction with the processor or other device.

As used herein, the term "module" can refer to either or both of: (i) a software component that causes an electronic device to accept various inputs and generate certain outputs; or (ii) an electronic input/output interface, such as a panel, frame, textbox, window or other portion of a GUI.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

We claim:

1. A method of training a neural network modeling physical phenomena of semiconductor material, wherein the method comprises:

receiving plurality of training pairs corresponding to a semiconductor material, wherein each training pair comprises an input charge to a distinct voxel of the semiconductor material and one or more output signals generated by the distinct voxel in response to the input charge;

training a neural network using the training pairs, wherein the neural network models the semiconductor material and each voxel is represented in the neural network by a tensor field defined by (i) a location of the voxel within the semiconductor material and (ii) one or more physics-based phenomena within the voxel at the location.

2. The method of claim 1, wherein the tensor field comprises a sub-tensor corresponding to transport of electrons and holes in the semiconductor material.

3. The method of claim 1, wherein the tensor field comprises a sub-tensor corresponding to trapping and de-trapping of electrons and holes in the semiconductor material.

4. The method of claim 1, wherein the tensor field comprises a sub-tensor corresponding to recombination of electrons and holes in the semiconductor material.

5. The method of claim 1, wherein the tensor field comprises a sub-tensor corresponding to diffusion of electrons and holes in the semiconductor material.

6. The method of claim 1, wherein the tensor field for the voxel comprises a plurality of sub-tensors and each sub-tensor corresponds to one of the physics-based phenomena.

7. The method of claim 6, wherein the plurality of sub-tensors are combined using mathematical operations to provide an output for the voxel in the neural network.

8. The method of claim 1, wherein each tensor field in the neural network is optimized during the training using a gradient descent algorithm based on a loss function.

9. The method of claim 8, wherein the loss function is a L2 norm of a difference between output signals in the training pairs and an estimated output signal generated using the tensor field.

10. A method of training a neural network modeling physical phenomena of a semiconductor material, wherein the method comprises:
receiving plurality of training pairs corresponding to a semiconductor material, wherein each training pair comprises an input charge to a distinct voxel of the semiconductor material and one or more output signals generated by the distinct voxel in response to the input charge;
training a neural network using the training pairs, wherein (i) the neural network comprises a plurality of weights transforming input data to nodes of the neural network and (ii) each of the weights models one or more physics-based phenomena related to the semiconductor material.

11. The method of claim 10, wherein one or more of the weights model transport of electrons and holes in the semiconductor material.

12. The method of claim 10, wherein one or more of the weights model trapping and de-trapping of electrons and holes in the semiconductor material.

13. The method of claim 10, wherein one or more of the weights model recombination of electrons and holes in the semiconductor material.

14. The method of claim 10, wherein one or more of the weights model diffusion of electrons and holes in the semiconductor material.

15. The method of claim 10, wherein the weights are modeled using a plurality of tensors and each tensor corresponds to one of the physics-based phenomena.

16. The method of claim 15, wherein the plurality of tensors corresponding to a node in the neural network are combined using mathematical operations to provide an output for the node.

17. The method of claim 10, wherein each of the weights is optimized during the training using a gradient descent algorithm based on a loss function.

18. The method of claim 17, wherein the loss function is a L2 norm of a difference between an output signal in the training pairs and an estimated output signal generated using the weights.

19. A method of training a neural network modeling physical phenomena of a semiconductor material, wherein the method comprises:
receiving an input charge measurement;
generating a voxel-by-voxel description of a semiconductor's material properties by applying the input charge measurement to a trained neural network, wherein (i) the trained neural network comprises a plurality of weights transforming input data to nodes of the trained neural network and (ii) each of the weights models one or more physics-based phenomena related to the semiconductor material; and
displaying at least a portion of the voxel-by-voxel description of the semiconductor's material properties in a graphical user interface.

* * * * *